(12) United States Patent
Seligmann

(10) Patent No.: US 7,013,003 B2
(45) Date of Patent: Mar. 14, 2006

(54) LOCATION-BASED FORWARDING

(75) Inventor: Doree Duncan Seligmann, New York, NY (US)

(73) Assignee: Avaya Technologies, Corp., Basking Ridge, NJ (US)

( * ) Notice: Subject to any disclaimer, the term of this patent is extended or adjusted under 35 U.S.C. 154(b) by 360 days.

(21) Appl. No.: 10/375,252

(22) Filed: Feb. 27, 2003

(65) Prior Publication Data

US 2004/0185838 A1    Sep. 23, 2004

Related U.S. Application Data

(60) Provisional application No. 60/380,140, filed on May 6, 2002.

(51) Int. Cl.
    *H04M 3/42* (2006.01)
(52) U.S. Cl. .............................. 379/211.02; 379/212.01
(58) Field of Classification Search ............ 379/211.02
    See application file for complete search history.

(56) References Cited

U.S. PATENT DOCUMENTS

| | | | |
|---|---|---|---|
| 5,428,663 A * | 6/1995 | Grimes et al. ............. | 340/7.21 |
| 5,481,590 A | 1/1996 | Grimes | |
| 5,790,974 A | 8/1998 | Tognazzini | |
| 5,938,721 A | 8/1999 | Dussell et al. | |
| 6,026,156 A | 2/2000 | Epler et al. | |
| 6,222,482 B1 | 4/2001 | Gueziec | |
| 6,356,533 B1 | 3/2002 | Bruno et al. | |
| 6,363,248 B1 * | 3/2002 | Silverman ................... | 455/417 |
| 6,411,687 B1 | 6/2002 | Bohacek et al. | |
| 6,434,404 B1 | 8/2002 | Claxton et al. | |
| 6,535,748 B1 | 3/2003 | Vuorio et al. | |
| 6,542,584 B1 | 4/2003 | Sherwood et al. | |
| 6,584,316 B1 * | 6/2003 | Akhteruzzaman et al. .. | 455/445 |
| 2002/0059434 A1 | 5/2002 | Karaoguz et al. | |
| 2002/0086680 A1 | 7/2002 | Hunzinger | |
| 2002/0089421 A1 | 7/2002 | Farringdon et al. | |
| 2003/0039339 A1 | 2/2003 | Luehrig et al. | |
| 2003/0054865 A1 | 3/2003 | Byers et al. | |

FOREIGN PATENT DOCUMENTS

| | | |
|---|---|---|
| EP | 1008946 | 6/2000 |
| GB | 2303271 A | 2/1997 |
| JP | 09113599 | 2/1997 |
| WO | WO 97/50231 | 12/1997 |

* cited by examiner

Primary Examiner—Creighton Smith
(74) Attorney, Agent, or Firm—DeMont & Breyer, LLC

(57) ABSTRACT

A method for enabling signals directed to a first telecommunications terminal to be forwarded to a second telecommunications terminal in the vicinity of the first terminal is disclosed. In particular, the illustrative embodiment automatically forwards signals to the closest telecommunications terminal for which the first terminal is authorized to do so.

21 Claims, 5 Drawing Sheets

LOCATION-BASED FORWARDING

STATEMENT OF RELATED APPLICATIONS

This application claims the benefit of U.S. Provisional Patent Application Ser. No. 60/380,140, filed on 6 May 2002, entitled "Method for Interception, Manipulations, and Usage of Bluetooth Voice Streams," which is also incorporated by reference.

CROSS-REFERENCE TO RELATED APPLICATIONS

The following patent applications are incorporated by reference:
1. U.S. patent application Ser. No. 10/375,663, filed 27 Feb. 2003, entitled "Authorization-Based Forwarding,";
2. U.S. patent application Ser. No. 10/375,271, filed 27 Feb. 2003, entitled "Server-Based Discovery For Location-Based Forwarding,";
3. U.S. patent application Ser. No. 10/375,641, filed 27 Feb. 2003, entitled "Peer-to-Peer Discovery For Location-Based Forwarding,"; and
4. U.S. patent application Ser. No. 10/375,237, filed 27 Feb. 2003, entitled "Location-Based Forwarding Over Multiple Networks,".

FIELD OF THE INVENTION

The present invention relates to telecommunications in general, and, in particular, to forwarding a call or message from one telecommunications terminal to another.

BACKGROUND OF THE INVENTION

Telephone calls are sometimes forwarded from one telephone to another. Consider FIG. 1, which depicts user 110 and user 115 in an office with respective wireline telephones 120 and 125. When user 110 leaves his or her office to work in a computer laboratory, for example, user 110 might forward his or her telephone to a telephone in the computer laboratory. User 110 thus specifies ahead-of-time that any future call directed to telephone 120 should be redirected to the telephone in the computer laboratory (i.e., a call directed to telephone 120 will cause the computer laboratory telephone to "ring," while telephone 120 will not ring).

As another example, when user 110 receives a call on telephone 120, he or she might wish to transfer the call to another telephone (e.g., a secretary's telephone, etc.) while the call is in progress. Alternatively, user 110 might wish to include another party (e.g., user 115, etc.) in the conversation by bridging the call to an appropriate telephone (e.g., telephone 125, etc.); this is also known as conference calling.

Forwarding is also commonly employed for email. In particular, a forwarding mechanism is established (e.g., creating a forward file in a UNIX-based system, etc.) so that future email messages addressed to a first address are automatically forwarded to a second address.

SUMMARY OF THE INVENTION

The present invention is a method for enabling signals (e.g., voice, video, text, etc.) directed to a first telecommunications terminal (e.g., telephone, computer, pager, etc.) to be forwarded to a second telecommunications terminal, which is or was in the "vicinity" of the first terminal. In particular, the illustrative embodiment automatically forwards signals directed to the first telecommunications terminal to the closest telecommunications terminal that the first telecommunications terminal is authorized to forward to.

The illustrative embodiment comprises: receiving a location of a first telecommunications terminal; ascertaining a second telecommunications terminal wherein: the second telecommunications terminal is within a distance threshold of the first telecommunications terminal, and the second telecommunications terminal is at least as close to the first telecommunications terminal as any other telecommunications terminal; and forwarding a signal directed to the first telecommunications terminal to the second telecommunications terminal.

DETAILED DESCRIPTION

Figure 1:
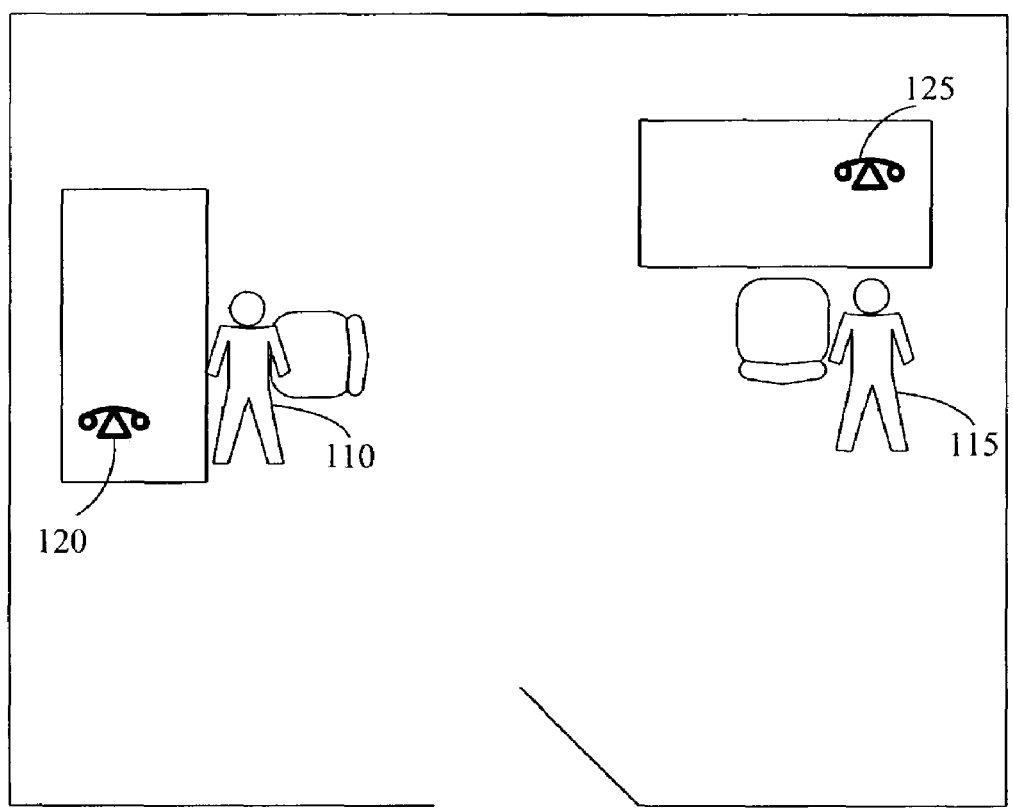
FIG. 1 is a representational diagram depicting an office with two users and two wireline telephones, in accordance with the prior art.

Definitions—Although the illustrative embodiment is disclosed in the context of telephones, it will be clear to those skilled in the art how to use embodiments of the present invention for other devices such as pagers, personal digital assistants (PDAs), etc. Consequently, the term "contact identifier" and its inflected forms are defined as a string of symbols that uniquely specifies a telecommunications terminal (e.g., telephone number, email address, Internet Protocol (IP) address, etc.). Similarly, for the purposes of this specification the term "call" is defined to encompass all kinds of communications (e.g. telephone call, email message, interactive text chat, videoconference, etc.), and it will be clear to those skilled in the art how to use embodiments of the present invention for such alternative means of communication.

For the purposes of this specification, the term "forwarding out" and its inflected forms are defined as forwarding a call from a first telecommunications terminal to a second telecommunications terminal as a result of a forwarding request originating at the first telecommunications terminal. Similarly, for the purposes of this specification the term "forwarding in" and its inflected forms are defined as forwarding a call from a first telecommunications terminal to a second telecommunications terminal as a result of a forwarding request originating at the second telecommunications terminal.

For some kinds of communication, such as telephone calls and interactive text chat, forwarding can be established either (i) before a call is initiated, or (ii) during a call (i.e., while a call is in progress). For some other kinds of communication such as email, however, forwarding typically applies to (i) only.

For case (i), a call can be forwarded from a first terminal to a second terminal so that either (ia) only the second terminal is notified of the incoming call (i.e., only the second terminal "rings"), or (ib) both the first and second terminals are notified of the incoming call (i.e., both terminals ring). For case (ii), a call can be forwarded from a first terminal to a second terminal so that either (iia) the first communications terminal no longer participates in the call (i.e., only the second terminal participates), or (iib) the first terminal still participates in the call (i.e., both terminals participate).

Consequently, for the purposes of this specification: the term "redirecting" and its inflected forms are defined as forwarding a call or message in accordance with (ia) above; the term "connecting" and its inflected forms are defined as forwarding a call or message in accordance with (ib) above; the term "transferring" and its inflected forms are defined as forwarding a call or message in accordance with (iia) above; and the term "bridging" and its inflected forms are defined as forwarding a call or message in accordance with (iib) above.

In addition, for the purposes of this specification: the term "redirecting out" and its inflected forms are defined as forwarding out a call or message in accordance with (ia) above; the term "connecting out" and its inflected forms are defined as forwarding out a call or message in accordance with (ib) above; the term "transferring out" and its inflected forms are defined as forwarding out a call or message in accordance with (iia) above; and the term "bridging out" and its inflected forms are defined as forwarding out a call or message in accordance with (iib) above.

Similarly, for the purposes of this specification: the term "redirecting in" and its inflected forms are defined as forwarding in a call or message in accordance with (ia) above; the term "connecting in" and its inflected forms are defined as forwarding in a call or message in accordance with (ib) above; the term "transferring in" and its inflected forms are defined as forwarding in a call or message in accordance with (iia) above; and the term "bridging in" and its inflected forms are defined as forwarding in a call or message in accordance with (iib) above.

Figure 2:
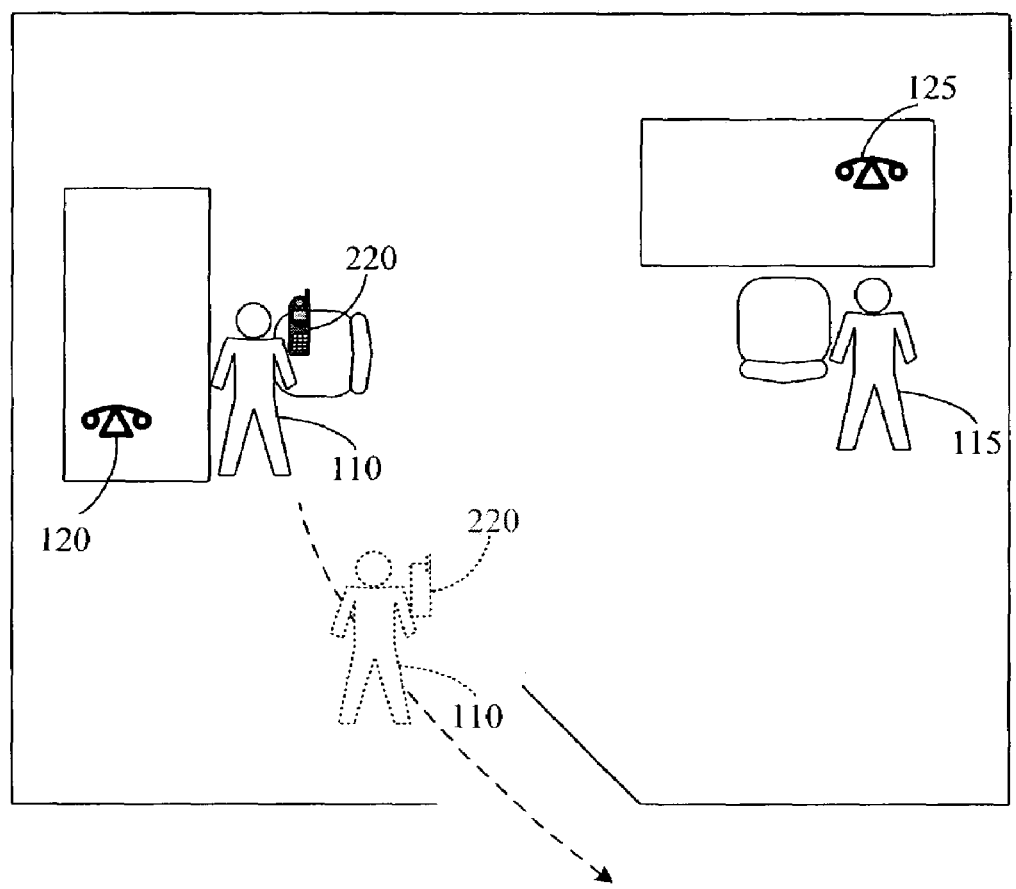
FIG. 2 is a representational diagram depicting user 110, as shown in FIG. 1, forwarding a call from wireline telephone 120, as shown in FIG. 1, to wireless telephone 220, in accordance with the illustrative embodiment of the present invention.
Figure 3:
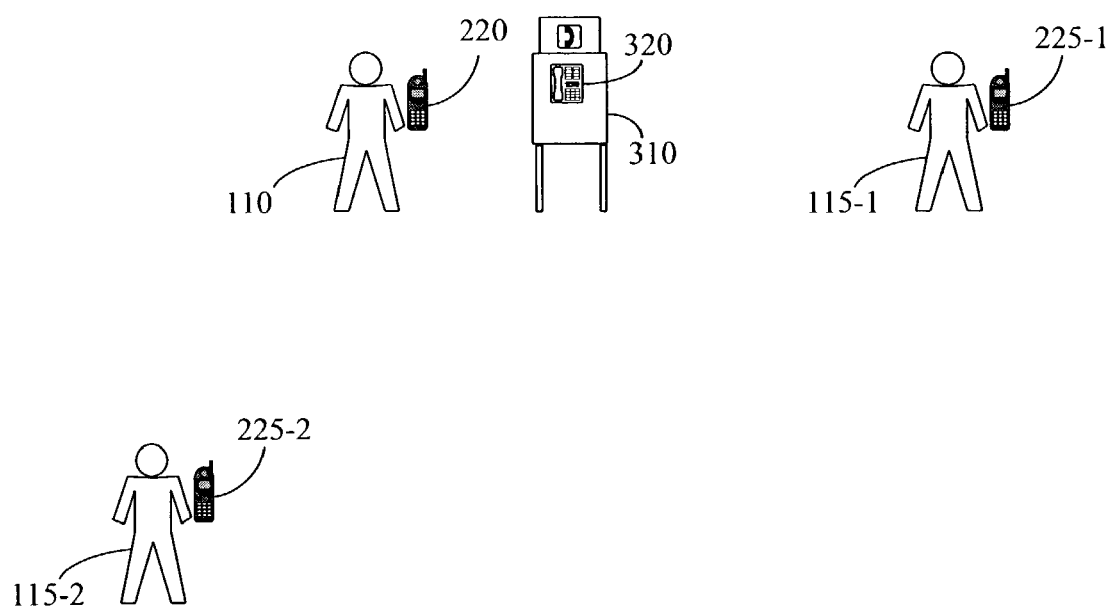
FIG. 3 is a representational diagram depicting user 110, as shown in FIG. 1, forwarding a call from wireless telephone 220, as shown in FIG. 2, to public phone booth telephone 320, in accordance with the illustrative embodiment of the present invention.
Figure 4:
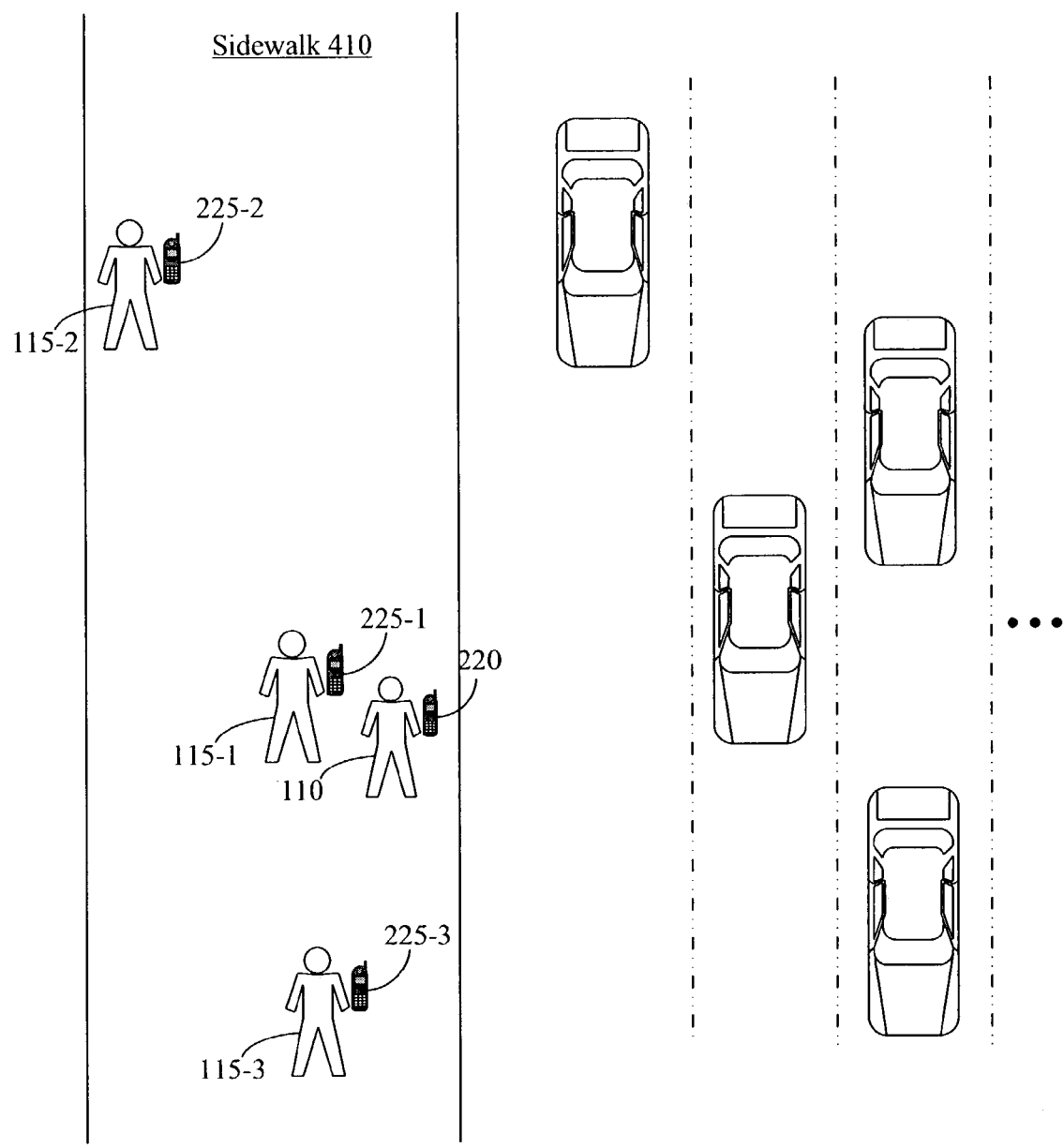
FIG. 4 is a representational diagram depicting user 110, as shown in FIG. 1, forwarding a call from wireless telephone 220, as shown in FIG. 2, to wireless telephone 225-1, in accordance with the illustrative embodiment of the present invention.

FIGS. 2 through 4 are representational diagrams illustrating how to make and use the illustrative embodiment of the present invention.

Redirect & Connect In—FIG. 2 depicts the elements of FIG. 1 (i.e., user 110 and user 115 with respective wireline telephones 120 and 125) with the addition of wireless telephone 220 belonging to user 110. As depicted in FIG. 2, user 110, prior to leaving the office, wishes to forward wireline telephone 120 to wireless telephone 220 so that he or she can receive calls to wireline telephone 120 while away from his or her office. In accordance with the illustrative embodiment of the present invention, user 110 indicates his or her wish simply by activating a "redirect in" function on wireless telephone 220 at a moment when wireline telephone 120 is the telecommunications terminal situated closest to wireless telephone 220 (i.e., closer to wireless telephone 220 than to wireline telephone 125, or to some wireless terminal on user 115's person, etc.), as is the case in FIG. 2 prior to user 110 leaving the office.

In accordance with the illustrative embodiment of the present invention, telephone calls directed to wireline telephone 120 after the "redirect in" function is activated will be redirected to wireless telephone 220 (i.e., wireless telephone 220, but not wireline telephone 120, will ring), even though user 110 did not input any information (e.g., contact identifier, etc.) specifying a terminal (e.g., wireline telephone 120, etc.) from which calls should be redirected. Thus, the present invention automatically enables redirecting based on the location of wireless telephone 220 and the locations of nearby telecommunications terminals.

In accordance with the illustrative embodiment of the present invention, a user alternatively might activate a "connect in" function. In the example above, telephone calls directed to wireline telephone 120 after the "connect in" function is activated will ring at both wireline telephone 120 and wireless telephone 220, as described in case (ib) above.

Distance Threshold—The illustrative embodiment of the present invention employs a distance threshold that defines the maximum distance at which forwarding to the closest telecommunications terminal can be established. In other words, if a user attempts to activate a telecommunications terminal's "redirect in" or "connect in" function when there are no other telecommunications terminals located within the distance threshold (e.g., five yards, etc.) of the user/terminal, then no forwarding occurs. Different values for the distance threshold result accordingly in different forwarding behavior. For example, a distance threshold of one inch effectively requires a user to "touch" one terminal to another to enable forwarding. Alternatively, a distance threshold of, say, five yards might be judged more desirable for some users and/or applications. In some embodiments the particular value of the distance threshold might be fixed, while in some other embodiments a user might be able to set/modify the value of the distance threshold or revert to a default value.

Redirect & Connect Out—In accordance with the illustrative embodiment of the present invention, in the scenario of FIG. 2 user 110 alternatively could have redirected telephone calls from office wireline telephone 120 to wireless telephone 220 by activating a "redirect out" function on wireline telephone 120 at a moment when wireless telephone 220 was the closest telecommunications terminal to wireline telephone 120, as was the case above when wireless telephone 220's "redirect in" function was activated. Similarly, activating a "connect out" function on wireline telephone 120 would work in the same fashion as activating "connect in" on wireless telephone 220. The distance threshold described above governs the operation of the "redirect out" and "connect out" functions in the same fashion as the "redirect in" and "connect in" functions.

Transfer Out & In—FIG. 3 depicts an alternative scenario in which user 110 is engaged in a telephone conversation, using wireless telephone 220, while walking down a city street populated with other users 115 holding respective wireless communications terminals 225. During the conversation, wireless telephone 220 issues a warning that its battery is low. User 110 walks towards payphone booth 310 and activates the "transfer out" function on wireless telephone 220, which causes the phone call to automatically transfer to pay telephone 320, the closest telecommunications terminal (as depicted in FIG. 3). User 110 picks up pay telephone 320 and continues the conversation, and wireless telephone 220 returns to its power-saving "standby mode", as is well-known in the art. (User 110, if he or she wishes to further save battery power, could turn off wireless telephone 220 completely as soon as the call was transferred to pay telephone 320.)

In accordance with the illustrative embodiment of the present invention, a "transfer in" function is also provided. The distance threshold governs the operation of the "transfer out" and "transfer in" functions as described above.

Bridge Out & In—FIG. 4 illustrates yet another example of the use of the illustrative embodiment of the present invention. In this example, user 110 is walking down a city street with his friend 115-1, while talking over wireless telephone 220 to his sister (e.g., giving directions to the theatre at which they are meeting in 30 minutes, etc.) The city street is populated with other users 115-2 and 115-3 carrying wireless telephones 225-2 and 225-3, respectively.

User 110, wishing to include user 115-1 in the conversation, activates a "bridge out" function on wireless telephone 220. In accordance with the illustrative embodiment of the present invention, "bridge out" functions in the same manner as "transfer out," except that the terminal that activates "bridge out" continues to participate in the telephone call, as connoted by the name of this function. Since user 110's friend 115-1's wireless telephone 225-1 is the closest terminal to wireless telephone 220 (as shown in FIG. 4), wireless telephone 225-1 is bridged into the call and user 115-1 can participate in the conversation via wireless telephone 225-1.

In accordance with the illustrative embodiment of the present invention, friend 115-1 alternatively could participate in user 110's conversation by activating a "bridge in" function on wireless telephone 225-1, since user 110's wireless telephone 220 is the closest terminal to friend 115-1's wireless telephone 225-1, as shown in FIG. 4. The distance threshold governs the operation of the "bridge out" and "bridge in" functions as described above.

Authorization—In the exemplary scenarios above, there is no mention of any authorization facility for granting or denying permission to forward a call to a particular telecommunications terminal. The illustrative embodiment of the present invention does, in fact, include such an authorization facility; a description of this facility was deferred until this point in the detailed description in the interest of clarity.

In order to illustrate why such a facility might be desirable, consider the scenario of FIG. 3. Suppose that at the moment user 110 activated the "transfer out" function, wireless telephone 220 was actually a little closer to wireless telephone 225-2, belonging to stranger 125-2, than pay telephone 320. Should the telephone call in fact be forwarded to wireless telephone 225-2? Clearly not, unless stranger 125-2 has, for some unusual reason, configured wireless telephone 225-2 to allow forwarding from a "strange" terminal.

Similarly, suppose stranger 125-2 activated the "transfer in" function on his or her wireless telephone 225-2 when 225-2 was the closest terminal to wireless telephone 220. Should wireless telephone 220 allow a strange terminal to "steal" an inprogress phone call from it? Again, clearly not, unless user 110 has, for some unusual reason, configured wireless telephone 220 to permit "forwarding in" requests from an arbitrary terminal.

The illustrative embodiment of the present invention employs the authorization facility disclosed in co-pending U.S. patent application Ser. No. 10/375663"Authorization-Based Forwarding,". This facility employs authorization tables associated with each telecommunications terminal to determine whether a particular forwarding attempt should be permitted. In the above-referenced U.S. patent application, the authorization tables are stored in a centralized database. In contrast, in the illustrative embodiment of the present invention, the authorization tables are stored in a distributed database system, wherein, as disclosed below in the descriptions of FIGS. 9 and 11, each node of the distributed database system is associated with a switch or base station.

In some other embodiments, an alternative technique might be used to enforce forwarding permissions. A wide variety of such techniques are well known in the art, and it will be clear to those skilled in the art how to incorporate such techniques into the illustrative embodiment of the present invention.

Figure 5:
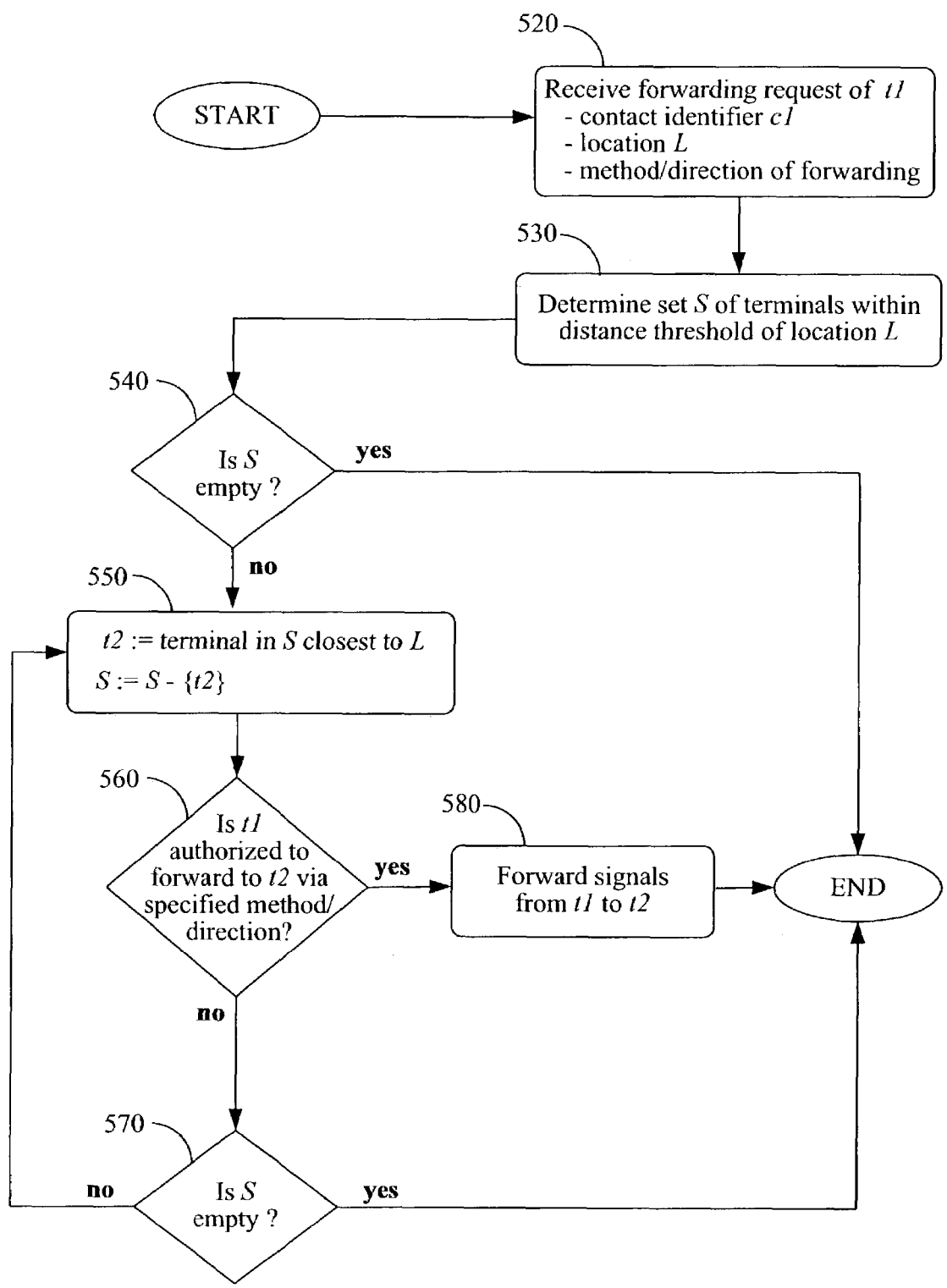
FIG. 5 depicts a flowchart of a method for processing a forwarding request, in accordance with the illustrative embodiment of the present invention.

FIG. 5 depicts a flowchart 500 of a method for processing a forwarding request, in accordance with the illustrative embodiment of the present invention. In particular, the method depicted in FIG. 5 accepts a forwarding request from a first telecommunications terminal and automatically forwards to the closest telecommunications terminal for which the first terminal is authorized to do so.

At task 520, a forwarding request from a first telecommunications terminal t1 is received. The forwarding request comprises: (1) the contact identifier c1 of terminal t1; (2) the location L of terminal t1; (3) the direction of forwarding (i.e., into or out of terminal t1); and (4) the method of forwarding (i.e., redirecting, connecting, transferring, or bridging).

At task 530, a set S of telecommunications terminals located within a distance threshold of location L is determined. The particular value of the distance threshold, as described above, might be chosen by the terminal provider or the user according to the desired behavior.

Task 540 checks whether set S, as determined in task 530, is empty. As shown in FIG. 5, if S is empty, then the method terminates; otherwise execution proceeds to task 550, disclosed below. Task 540 thus handles the case in which there are no other telecommunications terminals within the specified distance threshold to which to forward signals.

At task 550, the telecommunications terminal in S closest to L is determined; this terminal is stored in variable t2 and removed from set S. Two different apparatuses for performing task 550 are disclosed in co-pending U.S. patent applications Ser. No. 10/375271"Infrastructure For Location-Based Forwarding,", and Ser. No. 10/375,641 "Bluetooth For Location-Based Forwarding,".

Task 560 determines whether telecommunications terminal t1 is authorized to forward signals to telecommunications terminal t2. If so, execution proceeds to task 580, disclosed below; otherwise execution proceeds to task 570, disclosed below.

In the illustrative embodiment, task 560 is performed by consulting the appropriate authorization tables associated with terminals t1 and t2, as described above. It will be clear to those skilled in the art how to employ alternative authorization techniques in other embodiments.

Task 570 checks whether set S, as determined in task 550, is empty. As shown in FIG. 5, if S is empty, then the method terminates; otherwise execution returns to task 550 for the selection of another terminal from set S.

At task 580, a forwarding message is sent to establish forwarding from the telecommunications terminal t1 to telecommunications terminal t2. As is well understood in the art, for telephone calls the forwarding message is sent to the Public Switched Telephone Network (PSTN), and the PSTN routes the message to the appropriate switch, which causes: (i) the forward flag to be enabled in the record for the first telecommunications terminal's contact identifier (c1), and (ii) the forwarding number in this record to be set to terminal t2's contact identifier. For email messages, the forwarding message is sent over the Internet to the appropriate email server to establish forwarding of messages directed to c1 (i.e., terminal t1's email address) to terminal t2's email address, as is well understood in the art. For peer-to-peer communications employing the Session Initiation Protocol (SIP), such as instant messaging (IM), the forwarding message is an update message sent over the Internet to the appropriate SIP server for updating the contact identifier (i.e., IP address) associated with the user of terminal t1 to terminal t2's IP address, as is well understood in the art.

It is to be understood that the above-described embodiments are merely illustrative of the present invention and that many variations of the above-described embodiments can be devised by those skilled in the art without departing from the scope of the invention. It is therefore intended that such variations be included within the scope of the following claims and their equivalents.

The invention claimed is:

1. A method comprising:
   (a) receiving (i) a location of a first telecommunications terminal and (ii) a forwarding request from said first telecommunications terminal;
   (b) ascertaining the identity of a second telecommunications terminal, wherein said second telecommunications terminal is the closest telecommunications terminal to said first telecommunications terminal to which said first telecommunications terminal is authorized to have signals forwarded; and
   (c) forwarding a signal directed to said first telecommunications terminal to said second telecommunications terminal based on the receiving of said forwarding request.

2. The method of claim 1 wherein said forwarding is selected from the group consisting of: redirecting, transferring, bridging, and connecting.

3. The method of claim 1 wherein at least one of said first telecommunications terminal and said second telecommunications terminal is wireless.

4. The method of claim 1 wherein said ascertaining comprises:
   determining a set of telecommunications terminals within a distance threshold of said first telecommunications terminal, and
   selecting from said set the telecommunications terminal closest to said first telecommunications terminal.

5. The method of claim 4 wherein said ascertaining further comprises computing at least one distance between said first telecommunications terminal and a respective one of said telecommunications terminals in said set.

6. A method comprising:
   (a) receiving (i) a location of a first telecommunications terminal and (ii) a forwarding request from said first telecommunications terminal;
   (b) ascertaining the identity of a second telecommunications terminal, wherein said second telecommunications terminal is the closest telecommunications terminal to said first telecommunications terminal; and
   (c) forwarding a signal directed to said second telecommunications terminal to said first telecommunications terminal based on the receiving of said forwarding request.

7. The method of claim 6 wherein said forwarding is selected from the group consisting of: redirecting, transferring, bridging, and connecting.

8. The method of claim 6 wherein at least one of said first telecommunications terminal and said second telecommunications terminal is wireless.

9. The method of claim 6 wherein said ascertaining comprises:
   determining a set of telecommunications terminals within a distance threshold of said first telecommunications terminal, and
   selecting from said set the telecommunications terminal closest to said first telecommunications terminal.

10. The method of claim 9 wherein said ascertaining further comprises computing at least one distance between said first telecommunications terminal and a respective one of said telecommunications terminals in said set.

11. A method comprising:
    (a) receiving a forwarding request associated with a first telecommunications terminal;
    (b) ascertaining the identity of a second telecommunications terminal, wherein said second telecommunications terminal is the closest telecommunications terminal to said first telecommunications terminal to which said first telecommunications terminal is authorized to forward signals; and
    (c) forwarding a signal directed to said first telecommunications terminal to said second telecommunications terminal based on the receiving of said forwarding request.

12. The method of claim 11 wherein said forwarding is selected from the group consisting of: redirecting, transferring, bridging, and connecting.

13. The method of claim 11 wherein at least one of said first telecommunications terminal and said second telecommunications terminal is wireless.

14. The method of claim 11 wherein said ascertaining comprises:
    determining a set of telecommunications terminals within a distance threshold of said first telecommunications terminal, and
    selecting said second telecommunications terminal from said set.

15. The method of claim 14 wherein said selecting comprises rejecting a third telecommunications terminal, wherein:
    the distance between said third telecommunications terminal and said first telecommunications terminal is less than the distance between said second telecommunications terminal and said first telecommunications terminal, and
    said first telecommunications terminal is unauthorized to forward signals to said third telecommunications terminal.

16. A method comprising:
    (a) receiving a forwarding request associated with a first telecommunications terminal;
    (b) ascertaining the identity of a second telecommunications terminal, wherein said second telecommunications terminal is the closest telecommunications terminal to said first telecommunications terminal from which said first telecommunications terminal is authorized to receive forwarded signals; and
    (c) forwarding a signal directed to said second telecommunications terminal to said first telecommunications terminal based on the receiving of said forwarding request.

17. The method of claim 16 wherein said forwarding is selected from the group consisting of: redirecting, transferring, bridging, and connecting.

18. The method of claim 16 wherein at least one of said first telecommunications terminal and said second telecommunications terminal is wireless.

19. The method of claim 16 wherein said ascertaining comprises:

determining a set of telecommunications terminals within a distance threshold of said first telecommunications terminal, and selecting said second telecommunications terminal from said set.

20. The method of claim 14 wherein said selecting comprises rejecting a third telecommunications terminal, wherein:

the distance between said third telecommunications terminal and said first telecommunications terminal is less than the distance between said second telecommunications terminal and said first telecommunications terminal, and said first telecommunications terminal is unauthorized to receive forwarded signals from said third telecommunications terminal.

21. A method comprising:

(a) receiving (i) a location of a first telecommunications terminal and (ii) a forwarding request from said first telecommunications terminal;

(b) ascertaining the identity of a second telecommunications terminal, wherein said second telecommunications terminal is the closest telecommunications terminal to said first telecommunications terminal; and (c) forwarding a signal directed to said first telecommunications terminal to said second telecommunications terminal based on the receiving of said forwarding request, wherein said signal is associated with an incoming call.

* * * * *